(12) United States Patent
Nakamura (10) Patent No.: US 9,681,976 B2
(45) Date of Patent: Jun. 20, 2017

(54) INTERDIGITAL PAD

(71) Applicant: E-SMILE CO., LTD., Tokyo (JP)

(72) Inventor: Jun Nakamura, Tokyo (JP)

(73) Assignee: E-SMILE Co., Ltd., Setagaya-ku, Tokyo (JP)

( * ) Notice: Subject to any disclaimer, the term of this patent is extended or adjusted under 35 U.S.C. 154(b) by 0 days.

(21) Appl. No.: 14/404,981

(22) PCT Filed: Apr. 9, 2014

(86) PCT No.: PCT/JP2014/060280
§ 371 (c)(1),
(2) Date: Dec. 2, 2014

(87) PCT Pub. No.: WO2014/199710
PCT Pub. Date: Dec. 18, 2014

(65) Prior Publication Data
US 2016/0270942 A1 Sep. 22, 2016

(30) Foreign Application Priority Data

Jun. 11, 2013 (JP) .................................. 2013-123202

(51) Int. Cl.
*A61F 5/00* (2006.01)
*A61F 5/01* (2006.01)
*A61F 5/10* (2006.01)
*A61F 5/14* (2006.01)
*A61F 5/30* (2006.01)

(52) U.S. Cl.
CPC .............. *A61F 5/019* (2013.01); *A61F 5/10* (2013.01); *A61F 5/14* (2013.01); *A61F 5/30* (2013.01)

(58) Field of Classification Search
CPC ........ G06N 99/005; G06N 5/048; G06N 5/04; G06N 5/045; A61K 2300/00; A61K 31/19; A61K 31/191; A61K 31/192; A61K 31/194; A61K 31/375; A61K 31/60; A61K 33/00; A61K 45/06; A61K 47/36; A61K 9/0014; A61K 9/06; A61F 5/019; A61F 5/10
USPC .......................................................... 602/30
See application file for complete search history.

(56) References Cited

U.S. PATENT DOCUMENTS

| | | | | |
|---|---|---|---|---|
| 1,787,398 A * | 12/1930 | Sidgreaves | ............. | A61F 5/019 602/30 |
| 2,354,770 A * | 8/1944 | Patterson | ................ | A61F 5/019 602/30 |
| 2,471,997 A * | 5/1949 | Baltor | ..................... | A61F 5/019 132/73 |
| 2,531,851 A * | 11/1950 | Kiwad | ..................... | A43B 7/26 128/894 |

(Continued)

*Primary Examiner* — Michael Brown
(74) *Attorney, Agent, or Firm* — Sughrue Mion, PLLC (57) ABSTRACT

An interdigital pad for toes having a larger diameter engaging ring fitted on the big toe, a smaller diameter engaging ring fitted on the fourth toe, a base connecting said engaging rings and positioned on the sole of the foot, a projection fitted between and caught by the second and third toes, said base and two engaging rings forming an arched edge contacting the roots of respective toes, and a thickness of a lower ring of said larger diameter engaging ring and a thickness of the base of the second toe being thicker than a thickness of a portion located from the third to the fifth toes, so a height from the floor surface at a side of the little toe and fourth toe is a higher than at a side of the big toe.

6 Claims, 6 Drawing Sheets

(56) References Cited

U.S. PATENT DOCUMENTS 3,299,894 A * 1/1967 Charlebois ............ A61F 13/068
  36/140
2013/0190671 A1 * 7/2013 Pastore .................... A61F 5/10
  602/22

* cited by examiner

INTERDIGITAL PAD

CROSS REFERENCE TO RELATED APPLICATIONS

This application is a National Stage of International Application No. PCT/JP2014/060280 filed Apr. 9, 2014, claiming priority based on Japanese Patent Application No. 2013-123202 filed Jun. 11, 2013, the contents of all of which are incorporated herein by reference in their entirety.

TECHNICAL FIELD

This invention relates to an interdigital pad (or "inter-toes" pad) which is fitted or attached to the toes, with interposing "inter-toes pad portions" positioned between adjacent toes, for correcting an upright posture or a walking posture, so that a good posture can be maintained during walking and exercise and the efficiency of exercise is improved.

BACKGROUND ART

A variety of toe-pads have been proposed for a long time to arrange a pad between toes. For example, Patent Document No. 1 (JP-A1-2008-12077) proposes a toe pad for promoting blood circulation of toes by inserting pads between adjacent toes. In this toe pad, cylindrical pads bodies each of which is inserted between adjacent toes are tied by a strap. Patent Document No. 2 (Japanese Registered Utility Model No. 3,021,096) proposes a toe pad for enhancing antibacterial activity and for deodorizing the toes which are steamed inside shoes and for removing the discomfort caused by the sweat of toes. This toe pad is placed underside the base portion of toes but has four pads each having strip shape to be inserted between adjacent toes.

In these type toe pads, the pads are held between adjacent toes and come off easily. Therefore, Patent Document No. 3 (JP-A1-2007-313043) proposes to use a toe ring fitted on adjacent toes in addition to pads arranged between adjacent toes. This patent, however, provides an assistant tool for correction or prevention of deformation such as correction of hallux valgus.

The above-mentioned toe pads are used for promoting blood circulation of toes and for correction or prevention of deformation of toes but are not used for correcting the posture and for stabilizing a balance of body.

A tiptoe supporting pad used for stabilizing a balance of body is proposed in Patent Document No. 4 (Japanese Registered Utility Model No. 3,170,112). This tiptoe supporting pad is such a type that a tiptoe supporting pad is inserted or fit on the underside of the base of the toes and comprises a horizontal part arranged from an upper edge of the spherical contact surface of the foot sole to a lower side of the fingertip of at least second toe, third toe, fourth toe and fifth toe (little toe), and protrusions each entering into a space at least between second toe and third toe, between third toe and fourth toe and between fourth toe and little toe. The entirety of the tiptoe supporting pad has a gradually and smoothly curved shape in such a manner that an upper surface of the horizontal part and opposite side surfaces of the protrusions are united intimately with an underside of the base of respective toe.

LIST OF PRIOR ARTS

Patent Document

[Patent Document 1] JP-A1-2008-12077
[Patent Document 2] Japanese Registered Utility Model No. 3,021,096
[Patent Document 3] JP-A1-2007-313043
[Patent Document 4] Japanese Registered Utility Model No. 3,170,112

SUMMARY OF INVENTION

Problems to be Solved by the Invention

It is true that the tiptoe supporting pad disclosed in Patent Document No. 4 (Japanese Registered Utility Model No. 3,170,112) has a function to stabilize a balance of body but its ability for balancing the body is not sufficient. Still more, this tiptoe supporting pad having three protrusions has no interdigital pad between thumb and second toe. The biggest problem of the tiptoe supporting pad resides in that it falls off from the sole.

This invention was made to solve the above-mentioned problem and provides an interdigital pad which can stimulate all toes more moderately than the above-mentioned conventional tiptoe supporting pad. The interdigital pad according to the present invention permits to maintain a balance of the body by toes, to produce a firmly-standing force, to produce a force for holding the pad by toes, and to produce a force for keeping a good balanced posture, so that a proper or good posture can be maintained in walking and in exercise, resulting in that the efficiency of exercise is improved.

Means to Solve the Problem

In order to solve the above problem, the present invention provides, an invention of claim 1 provides an interdigital pad (or inter-toes pad) made of elastomer material having elasticity or stretchability and flexibility, characterized by a larger diameter engaging ring part to be fitted on the big toe and providing an interdigital pad portion positioned between the first toe and the second toe or index finger, a smaller diameter engaging ring part to be fitted on the fourth toe and providing an interdigital pad portion positioned between the third toe and the fifth toe or little toe, a base part connecting said engaging ring parts and to be positioned on the sole of the foot, a projected part integrated with said base part, and functioning as an interdigital pad portion when the projected part is fitted between the second toe and third toe, and being caught by the second for and third toe, each of the interdigital pad portions being positioned respectively between adjacent toes of all of five toes, the base part and two engaging ring parts forming an arched edge which contacts with the roots of respective toes at a side from which the toes are inserted into the engaging ring parts, a thickness of a lower ring portion of the larger diameter engaging ring par and a thickness of the base part of the second toe being thicker than a thickness of a portion located from the third toe to the fifth toe, so that a height from the floor surface at a side of the little toe and forth toe is a little higher than at a side of the big toe.

An invention of claim 2 is an interdigital pad according to claim 1, wherein the elastomer material is styrene type expandable elastomer An invention of claim 3 is an interdigital pad according to claim 1 or 2, wherein the elastomer material contains silver type inorganic antibacterial agent.

Advantages of the Invention

In the interdigital pad according to claim 1, an interdigital pad portion is positioned between adjacent toes of all of five toes, so that all toes are stimulate more moderately, the toes maintain a balance of body, a firmly-standing force is generated, and a force for holding the pad by toes is generated. In particular, since a thickness (h2) of a portion located from the third toe (c) to the fifth toe (e) is designed to be thicker than a thickness of a lower ring portion of the larger diameter engaging ring part and a thickness (h1) of the base part of the second toe, one's weight is put on the inner thigh, resulting in that a tendency of bow legs which is common for Japanese people can be corrected to a tendency of knock knees and a force to keep a good balanced posture is produced.

Still more, an arched edge is formed on the base part and two engaging ring parts which contacts with the roots of respective toes at a side from which the toes are inserted into said engaging ring parts, so that the toe pad can be positioned stably under the root portions of the toes and the impact transferred to the foot can be reduced, thereby strong pain of gonalgia and coxalgia can be eased. Therefore, the good posture in walking and in excises can be kept and the efficiency of excises can be improved, resulting in that the fatigue of body such as fatigue of necks and shoulders can be reduced just fitting the toe pad of the present invention.

In the invention of the interdigital pad according to claim 2, the elastomer was made of styrenic elastomer which have high elastic property, so that most sizes of the interdigital pad according to the present invention fit almost man and woman.

In the invention of the interdigital pad according to claim 3, the elastomer material contains antibacterial and deodorization properties, so that the product of the present invention is a sanitary interdigital pad.

MODE FOR CARRYING OUT THE INVENTION

Now, a preferable Example of the interdigital pad according to the present invention will be described with reference to drawings.

Example 1

Figure 1:
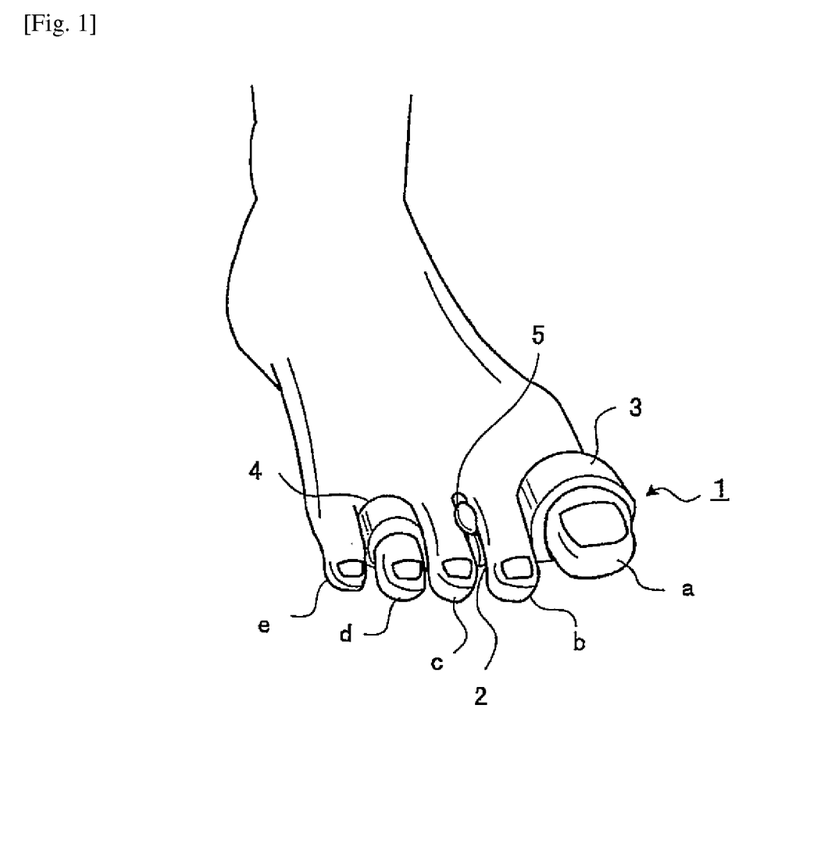
FIG. 1 A perspective view of the interdigital pad to be fitted on the right foot toe according to the present invention.

FIG. 1 is a perspective view of an example of the interdigital pad (1) for the right foot toe according to the present invention, illustrating a condition that the interdigital pad (1) is fitted on the right foot toe. The example of the interdigital pad (1) for the right foot toe according to the present invention is made of styrene type elastomer and possesses sufficient elasticity, flexibility and resiliency, so that most sizes of the interdigital pad according to the present invention fit almost man and woman. The elastomer material contains silver inorganic antibacterial agent, so that the product of the present invention is a sanitary interdigital pad having a deodorization property.

Figure 2:
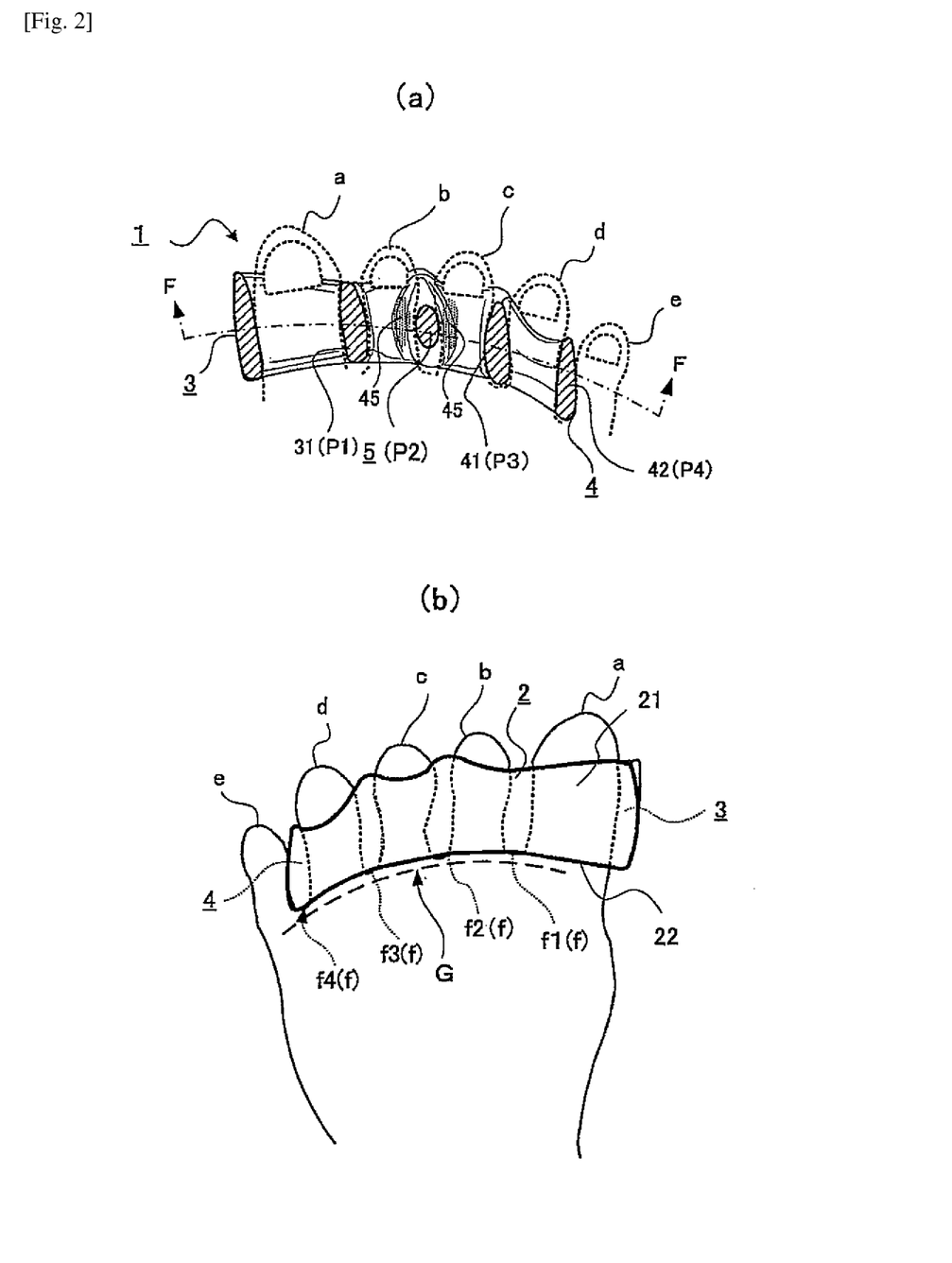
FIG. 2(a) is a cross section of FIG. 1 illustrating a condition when the interdigital pad is fitted on the right foot toe.
FIG. 2(b) is a rear view of the interdigital pad fitted on the right foot toe.

As is shown in FIG. 1 and FIG. 2(a), when the pad is used, a larger diameter engaging ring part (3) is fitted on the big toe of the first toe (a) and a smaller diameter engaging ring part (4) is fitted on the fourth toe (d), as well as a projected part (5) integrated with the base part (2) is fitted or inserted between the second toe (b) and third toe (c) or the projected part (5) is caught by the second toe (b) and third toe (c). FIG. 2 illustrates this condition.

FIG. 2(a) is a cross section showing a condition at an intermediate height level when the interdigital pad (1) is fitted on the right foot toe. As is shown in FIG. 2(a), a side portion (31) of the larger diameter engaging ring part (3) is positioned between the first toe (a) and the second toe (b) and is functioned as an interdigital pad, the projected part (5) is positioned between the second toe (b) and the third toe (c) and is functioned as an interdigital pad, a side portion (41) of the smaller diameter engaging ring part (4) is positioned between the third toe (c) and the fourth toe (d) and is functioned as an interdigital pad, and another side portion (42) of the smaller diameter engaging ring part (4) is positioned between the fourth toe (d) and the fifth toe (e) and is functioned as an interdigital pad. Therefore, all of five toes are separated by respective interdigital pad or each interdigital pad intervenes between adjacent toes.

How to fit the interdigital pad (1) according to the present invention and its placement positions will be explained with reference to FIG. 2(b) which illustrates a rear view of the interdigital pad fitted on the right foot toe. The base part (2) of pad of the interdigital pad (1) according to the present invention has an almost horizontally flat sole surface (21) which contacts with the floor. The larger diameter engaging ring part (3) and the smaller diameter engaging ring part (4) are arranged at opposite sides of the base part (2) on its upper surface. A fitting arch portion (22) is formed along a root arch (G) at a side where the root portion (f) of the interdigital pad (1) contacts with root portions (f1, f2, f3, f4) of respective toes.

In use, firstly, the larger diameter engaging ring part (3) is fitted on the first toe (big toe) (a) and then the smaller diameter engaging ring part (4) is fitted on the fourth toe (d) while the interdigital pad (1) is inserted deeply in such a manner that the fitting arch portion (22) is arranged along the four root portions (f1, f2, f3, f4).

Now, constituent elements of the interdigital pad (1) will be explained in details by using FIG. 3 to FIG. 9.

Figure 3:
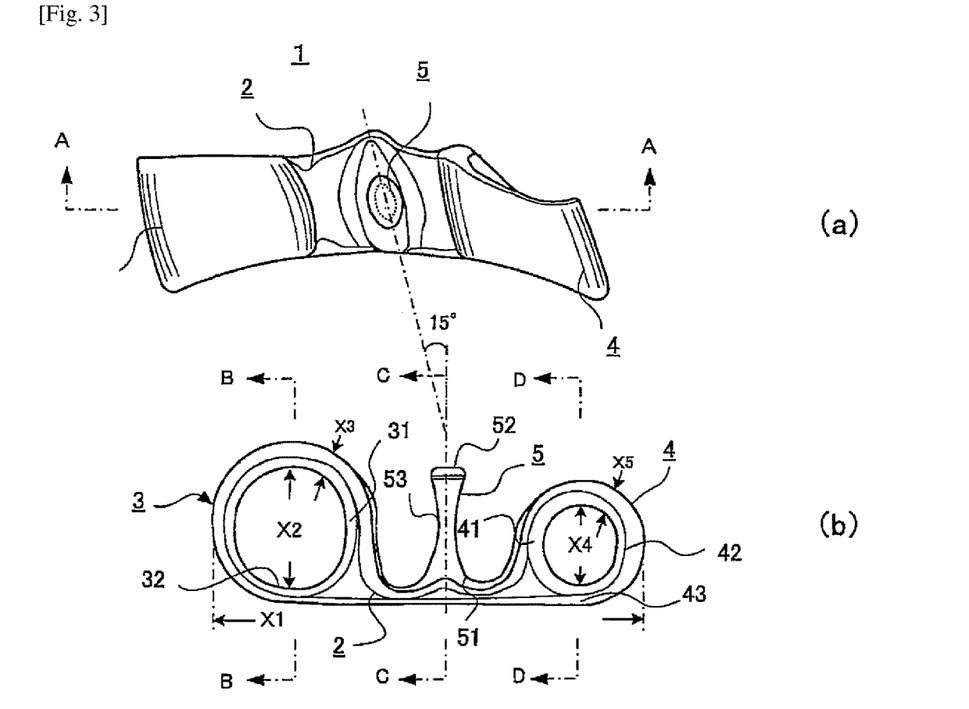
FIG. 3(a) is a plan view of the interdigital pad to be fitted on the right foot toe according to the present invention.
FIG. 3(b) is a front view of the interdigital pad of FIG. 3(a) which is tilted at an angle of 15°.
Figure 4:
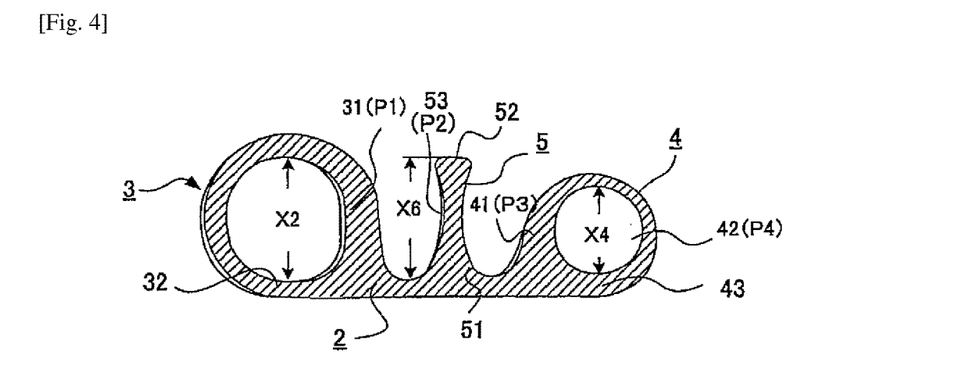
FIG. 4 A vertical cross sectional viewed along a line A-A in FIG. 3(a).
Figure 5:
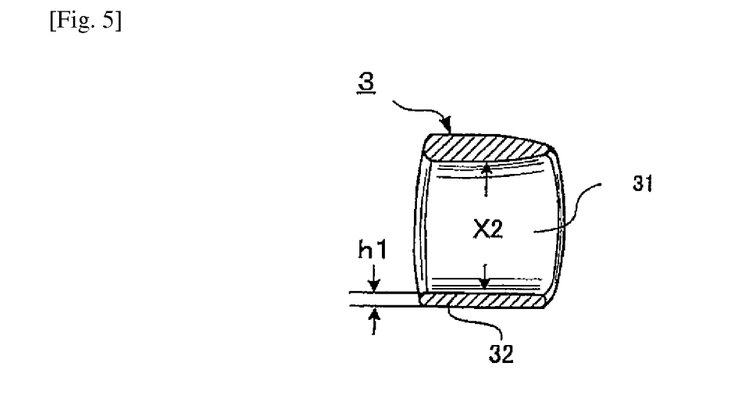
FIG. 5 A vertical cross sectional viewed along a line B-B in FIG. 3(b).

FIG. 3(a) is a plan view of the interdigital pad to be fitted on the right foot toes according to the present invention and FIG. 3(b) is a front view of the interdigital pad viewed at a tilted angle of 15° from a position of FIG. 3(a). All toes extend along the same direction but roots of four toes other than the first toe are not aligned horizontally with a root of the first toe and are inclined at an angle of 15° in average with respect to a root of the first toe. Therefore, the roots of four toes other than the first toe are positioned at an inclined at an angle of 15° as is shown in FIG. 3, so that the interdigital pad (1) according to the present invention fits to the toes comfortably A width (X1) of the interdigital pad (1) according to the present invention from the first toe to the fourth toe is 69.26 mm. Larger and smaller sizes other than this size can be prepared, in the same manner as shoe sizes.

The larger diameter engaging ring part (3) for the first toe or big toe (a) is positioned at a left side end of the base part (2). The larger diameter engaging ring part (3) is fitted on the first toe or big toe (a), so that the first toe or big toe (a) is surely fixed in interdigital pad (1) according to the present invention. A side portion (31) of the larger diameter engaging ring part (3) forms an interdigital pad portion (P1) which is positioned between the first toe (a) and the second toe (b). An inner diameter of the larger diameter engaging ring part (3) is explained in FIG. 3 and FIG. 5 in which X2 is about 16 mm and X3 which is a thickness of the side portion (31) is about 3 mm. As explained above, the interdigital pad (1) according to the present invention is made of silicon elastomer material possessing elasticity, flexibility and resiliency, so that the larger diameter engaging ring part (3) can be attached or fitted for all average person. The side portion (31) of the larger diameter engaging ring part (3) functions as an interdigital pad portion (P1).

The inner diameter of the larger diameter engaging ring part (3) is not limited to the above mentioned value of X2=16 mm but can be selected properly in a range of 14 mm to 20 mm in such a manner that a person wearing the interdigital pad (1) according to the present invention does not feel the pain.

Figure 9:
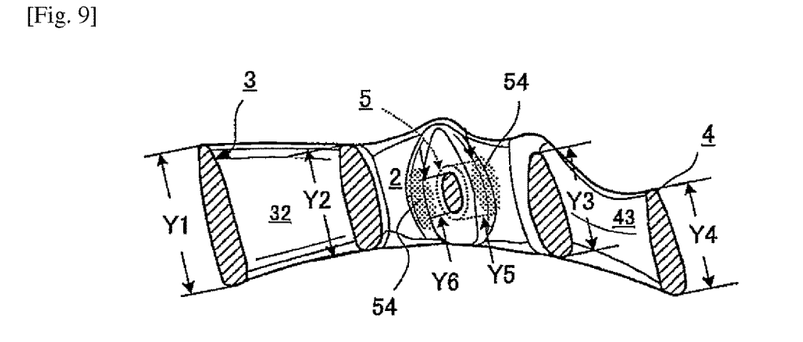
FIG. 9 A horizontal cross sectional viewed along a line E-E in FIG. 8.

As is shown in FIG. 9, an outside width Y1 of the larger diameter engaging ring part (3) is Y1=about 20 mm, while an inside width Y2 thereof which contacts with the second toe (b) is Y2=about 15 mm.

As is shown in FIG. 3(b), the smaller diameter engaging ring part (4) for the fourth toe (d) is positioned at a right side end of the base part (2). The smaller diameter engaging ring part (4) is fitted on the fourth toe (d), so that the interdigital pad (1) according to the present invention is fixed to toes more surely by this engagement together with the above engagement with the first toe (a).

A side portion (41) of the smaller diameter engaging ring part (4) forms another interdigital pad portion (P3) which is positioned between the third toe (c) and the fourth toe (d), while an opposite side portion (42) of the smaller diameter engaging ring part (4) forms further interdigital pad portion (P4) which is positioned between the forth toe (d) and the fifth toe or small toe (e).

Figure 7:
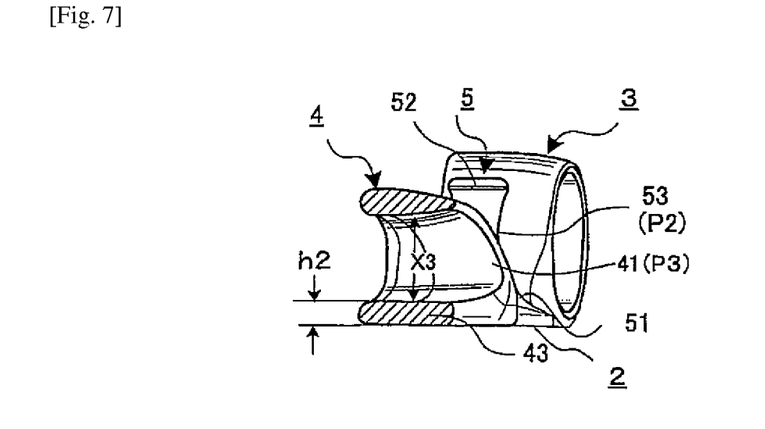
FIG. 7 A vertical cross sectional viewed along a line D-D in FIG. 3(b).

An inner diameter of the smaller diameter engaging ring part (4) is shown in FIG. 3 and FIG. 7 in which X4 is about 11 mm and X5 which is a thickness of the side portion (41) is about 5 mm. As explained above, the interdigital pad (1) according to the present invention itself is made of silicon elastomer material possessing elasticity, flexibility and resiliency, so that the smaller diameter engaging ring part (4) can be attached or fitted for all average person. The side portions (41, 2) of the smaller diameter engaging ring part (4) function as other interdigital pad portions (P3, P4).

The inner diameter of the smaller diameter engaging ring part (4) is not limited to the above mentioned value of X4=11 mm but can be selected properly in a range of 9 mm to 16 mm in such a manner that a person wearing the interdigital pad (1) according to the present invention does not feel the pain.

As is shown in FIG. 9, a width (Y3) of the smaller diameter engaging ring part (4) which contacts with the third toe (d) is Y3=about 15 mm, and a width (Y4) thereof which contacts with the fifth toe (e) is also Y4=about 15 mm.

As is shown in FIG. 2 and FIG. 3, the base part (2) has a horizontally flat sole surface (21) positioned at the underside of the foot and connecting the smaller diameter engaging ring part (4) to the larger diameter engaging ring part (3) positioned at opposite ends. The projected part (5) extends upwards from the base part (2) to form further interdigital pad portion (P2) which is held or clamped by the second toe (b) and third toe (c). In other words, the second toe (b) and third toe (c) are fitted to the projected part (5).

A fitting arch portion (22) is formed in the base part (2) at a part of the interdigital pad (1) which contacts with roots (f) of toes and extends along a fitting arch (G) drawn by respective toe root portions (f1, f2, f3, f4). As is shown in FIG. 10, the root arch (G) is formed also in a cross section cut along a line F-F in FIG. 2 (a) along toes, so that the interdigital pad (1) according to the present invention fits to the sole when a person wears the interdigital pad (1).

Figure 6:
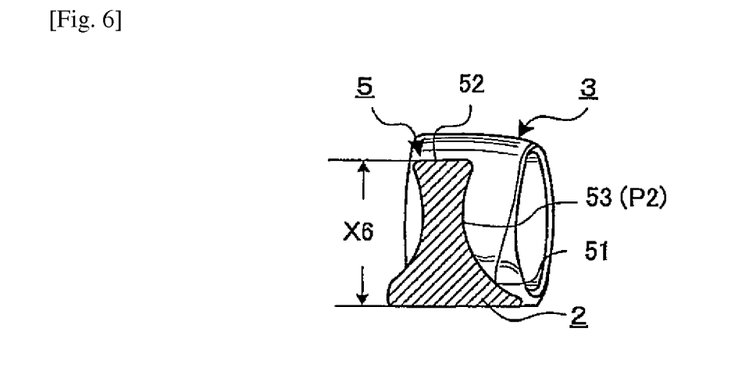
FIG. 6 A vertical cross sectional viewed along a line C-C in FIG. 3(b).

As is shown in a cross sectional view of FIG. 6, a height of the projected part (5) extending upwards from the base part (2) is about X6=9 mm to 16 mm. The projected part (5) has larger cross sectional areas at its bottom portion (51) and top portion (52) and has a slender or narrow intermediate portion (53) therebetween, so that the second toe and third toe are fixed at the narrow portion. As is shown in FIG. 9, a width Y5 of the projected part (5) at the bottom portion is Y5=about 8 mm, while a width Y6 of the projected part (5) at the narrow portion is Y6=about 6 mm.

Figure 8:
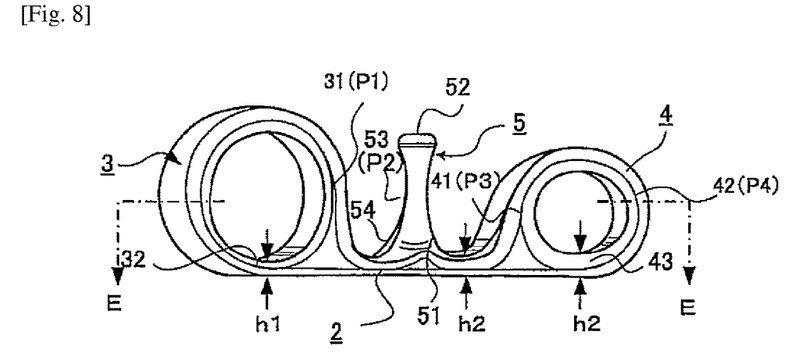
FIG. 8 A front view of the interdigital pad of FIG. 3(a) in a no-tilted condition.
Figure 10:
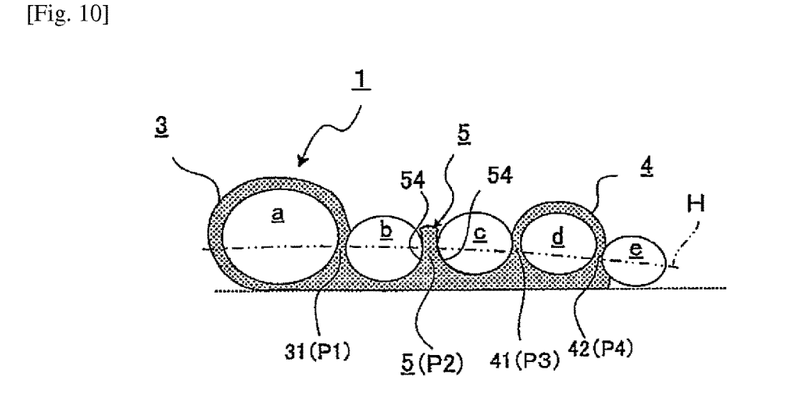
FIG. 10 A horizontal cross sectional viewed along a line F-F in FIG. 2(a).

As is shown in FIG. 8, FIG. 9 and FIG. 10, The projected part (5) has swollen or convex area (54) having a thicker inward wall in a region from the bottom portion (51) to the intermediate portion (53), resulting in that a transverse arch (H) is formed as is shown in FIG. 10. Owing to this configuration, a user wearing the interdigital pad (1) according to the present invention feels good or comfort, a firmly-standing force is created because a force is put onto the fingertips, and the worn interdigital pad (1) fits good beneath the sole.

The interdigital pad (1) according to the present invention has such a height or thickness from a floor or ground that a height (h2) in a region from the third toe (c) to the fifth toe (e) becomes a little thicker than a region of the first toe or big to (a). In fact, as is shown in FIG. 8, a height (h1) of from a lower ring portion of the larger diameter engaging ring part (3) for the first toe (a) to the second toe (b) is in a range of 1.5 mm to 2.5 mm, while a height (h2) in a region from the third toe (c) to the fifth toe (e) is in a range of 2.5 mm to 4 mm. In case of the present example, (h1) is 2 mm and (h2) is 3 mm. Owing to this design, one's weight is put on the inner thigh, so that a bow-legs tendency of Japanese can be corrected smoothly or easily to knock knee tendency. Still more, a firmly-standing force or endurance force is created because a force is put onto the fingertips since the transverse arch (H) shown in FIG. 10 is formed, resulting in that a force for keeping a good balanced posture is created.

The interdigital pad (1) according to the present invention of this example is made of a material possessing elasticity, flexibility and resiliency, in particular styrenic elastomer having high elastic property. Other synthetic resin materials having elasticity, flexibility and resiliency such as styrene rubber, polyurethane, polyvinylchloride, polyethylene, EVA, viscose sponges can be used provided that it is suitable for human skin.

In the example, the elastic material contains silver inorganic antibacterial agent. Other additives such as antibacterial agents, deodorants, disinfectants, antifungal agent and anti-trichophyton bacteria agent can be added to the elastic material in place of the silver inorganic antibacterial agent. The elastic material can contain further placenta and collagen to make the skin of toes beautiful, and contain further black silica and germanium to improve the blood circulation.

Figure 11:
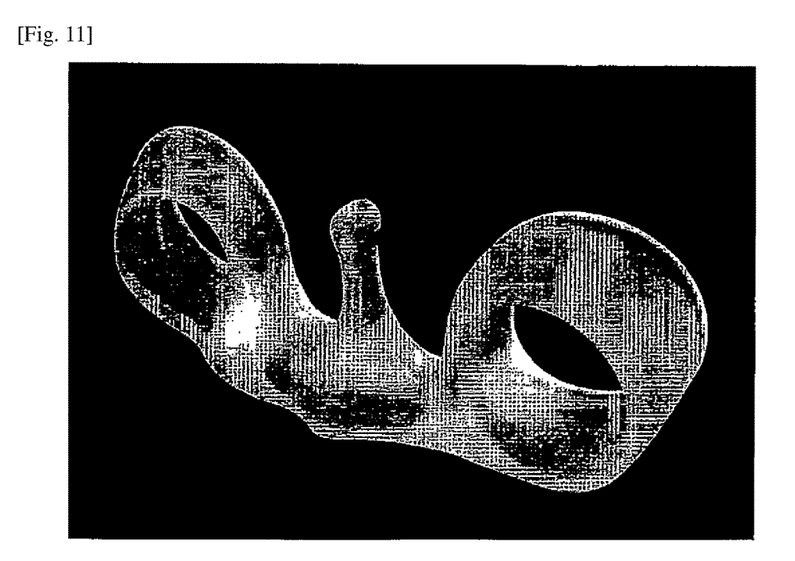
FIG. 11 A photograph of the interdigital pad according to the present invention took from the oblique above.

FIG. 11 is a photograph of an embodiment of the interdigital pad according to the present invention took from the oblique above. In this example, the interdigital pad is colorless translucent but can be colored to a skin color or pink and/or high fashionability can be given to the pad. The interdigital pad according to the present invention fits naturally to toes without uncomfortable feeling.

In this example, the interdigital pad (1) according to the present invention is explained for right foot. Explanation of the interdigital pad (1) for left foot is not described here, because it becomes the left-right symmetry.

In the example of the interdigital pad (1) according to the present invention, four interdigital pad portions (P1), (P2), (P3) and (P4) are positioned or intervene for all of five toes, so that all of these five toes are moderately stimulated, the toes maintain a balance of the body to create the firmly-standing force, and clamping forces to hold the pad (1) in the toes is produced. In particular, the thickness (h2) in a region from the third toe (c) to the fifth toe (e), namely a thickness of the lower ring portion of the smaller diameter engaging ring part (4), a thickness of fourth toe (d) and a thickness of third toe (c) is a little thicker than the thickness (h1) of the lower ring portion of the larger diameter engaging ring part (3) and a thickness of the second toe, the fifth toe side is elevated at a little higher position from the floor or ground than the first toe side. Owing to this design, a bow-legs tendency of Japanese can be corrected smoothly or easily to knock knee tendency and a force for keeping a good balanced posture is created.

Still more, the base part (2) and the larger and smaller diameter engaging ring parts (3, 4) are formed into a shape of a fitting arch portion (22) contacting with root portions of toes at a side where the interdigital pad (1) according to the present invention is inserted into toes, so that the interdigital pad (1) is fixed stably under the sole. Thus, the root arch portion (G) in the sole is stabilized, so that a firmly-standing force can be created, resulting in that the impact on the foot in the walking is eased and strong pain in gonalgia and coxalgia can be eased.

In fact, just only fitting the interdigital pad (1) according to the present invention, a sensitivity of toes becomes more delicate, one can grasp the ground easily and the sense of balance is improved, and hence the motor nerve is improved. Still more, the posture is corrected naturally and gradually along with development of the muscles plantaris which is a base of the body. The fatigue of neck and shoulder can be reduce since the center of gravity of the body is normalized when the user stands firmly by the toes on the ground, and the burden applied to the neck or the shoulders is reduced since the position of neck is raised and hence one can get a good style or figure. Still more, gonalgia is reduced and hip joint is improved, because the impact in the walking can be absorbed and the body balance in right and left as well as back and forward, resulting in that unnecessary force will not exerted onto the knee. Fatigue is reduced in case of standing work. The fatigue of the waist also can be reduced because the center of gravity of the body is normalized and the waist is supported in a right position and because the impact on the waist is reduced.

In this manner, good posture can be kept during walking and exercises and the efficiency in exercise is improved. As a result, the fatigue of necks and shoulders of the body can be reduced simply by fitting the interdigital pad (1) according to the present invention onto right and left toes.

The present invention is not limited to above Example but covers all variations which do not impair the characteristics of this invention.

REFERENCE NUMBERS a First toe (big toe),
b, Second toe (index finger),
c Third toe (middle finger)
d Fourth toe (ring finger)
e Fifth toe (little toe)
f, f1, f2, f3, f4 Root or base portions
G Root arch portion
H Transverse arch
P1, P2, P3, P4 Interdigital pad portion
1 Interdigital pad (inter-toes pad)
2 Base part
21 Sole surface
22 Arched edge
3 Larger diameter (circular) engaging ring part
31 Side portion
32 Lower ring portion
4 Smaller diameter (circular) engaging ring part
41 Side portion
42 Opposite side portion
43 Lower ring portion
5 Projected part
51 Root portion
52 Upper portion
53 Intermediate part
54 Root projected portion

The invention claimed is:
1. An interdigital pad for toes, made of an elastomer material having elasticity and flexibility, comprising,
a larger diameter engaging ring part to be fitted on the big toe or first toe and providing an interdigital pad portion positioned between the first toe and the second toe or index finger,
a smaller diameter engaging ring part to be fitted on the fourth toe and providing an interdigital pad portion positioned between the third toe and the fifth toe or little toe,
a base part connecting said engaging ring parts and to be positioned on the sole of the foot, and
a projected part integrated with said base part, said projected part functioning as an interdigital pad portion when the projected part is fitted between the second toe and third toe, and being caught by the second toe and third toe,
each of said interdigital pad portions being positioned respectively between adjacent toes of all of five toes, said base part and two engaging ring parts forming an arched edge which contacts with the roots of respective toes at a side from which the toes are inserted into said engaging ring parts, a thickness of a lower ring portion of said larger diameter engaging ring part and a thickness of the base part in a region of the big toe or first toe has a thickness h1 and a thickness of a lower ring portion of said smaller diameter engaging ring and the base part in a region between the third toe and the fifth toe has a thickness h2, wherein h1<h2.

2. The interdigital pad for toes according to claim 1, wherein said elastomer material is styrene type expandable elastomer.

3. The interdigital pad for toes according to claim 1, wherein said elastomer material contains silver type inorganic antibacterial agent.

4. The interdigital pad for toes according to claim 2, wherein said elastomer material contains silver type inorganic antibacterial agent.

5. The interdigital pad for toes according to claim 1, wherein the thickness of h2 is a little thicker than h1.

6. The interdigital pad for toes according to claim 5, wherein h1 is in a range of 1.5 mm to 2.5 mm and h2 is in range of greater than 2.5 mm to 4 mm.

* * * * *